(12) United States Patent
Huang et al.

(10) Patent No.: US 11,740,171 B2
(45) Date of Patent: Aug. 29, 2023

(54) OPEN-ENDED HOLLOW COAXIAL CABLE RESONATOR SENSOR

(71) Applicants: Jie Huang, Rolla, MO (US); Chen Zhu, Rolla, MO (US); Rex E. Gerald, II, Willow Springs, IL (US)

(72) Inventors: Jie Huang, Rolla, MO (US); Chen Zhu, Rolla, MO (US); Rex E. Gerald, II, Willow Springs, IL (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 354 days.

(21) Appl. No.: 17/209,785

(22) Filed: Mar. 23, 2021

(65) Prior Publication Data

US 2021/0310928 A1    Oct. 7, 2021

Related U.S. Application Data

(60) Provisional application No. 62/993,277, filed on Mar. 23, 2020.

(51) Int. Cl.
*G01N 15/06* (2006.01)
*G01N 33/497* (2006.01)
*G01N 1/24* (2006.01)

(52) U.S. Cl.
CPC .......... *G01N 15/0656* (2013.01); *G01N 1/24* (2013.01); *G01N 15/0618* (2013.01);
(Continued)

(58) Field of Classification Search
CPC ............ G01N 15/0656; G01N 1/24; G01N 15/0618; G01N 33/497; G01N 2001/245; G01N 2033/4975; G01N 15/0606
See application file for complete search history.

(56) References Cited

U.S. PATENT DOCUMENTS

| 3,594,657 A * | 7/1971 | Cook ............... H03B 29/00 257/664 |
| 2008/0282772 A1* | 11/2008 | Petinarides .......... G01N 1/24 73/31.02 |
| 2014/0015548 A1* | 1/2014 | Naughton ......... G01N 33/5438 29/829 |

OTHER PUBLICATIONS

Zhu, Chen, et al., Highly sensitive open-ended coaxial cable-based microwave resonator for humidity sensing, Elsevier, Sensors and Actuators A: Physical, Aug. 3, 2020, 7 pages, Rolla, Missouri United States.

(Continued)

*Primary Examiner* — David Z Huang
(74) *Attorney, Agent, or Firm* — Stinson LLP

(57) ABSTRACT

An open-ended hollow coaxial cable resonator probe configured to receive an aerosol sample for analysis. A metal post shorts the resonator's inner and outer conductors. A metal plate is spaced apart from an open end of the resonator by a dielectric layer that contains the received aerosol sample. Interrogator circuitry coupled to the resonator transmits an electromagnetic wave within the resonator and generates an electric field at the open end of the resonator. The interrogator circuitry is responsive to the generated electric field for determining a resonance frequency and an impedance of the resonator when the aerosol sample is present in the dielectric layer and is configured to identify virus particles in the aerosol sample as a function of the determined resonance frequency and impedance. A portable aerosol analyzer comprises the open-ended hollow coaxial cable resonator and a mouthpiece through which a subject expels a breath sample into the open end of the resonator. Antibodies tethered to high-permittivity nanoparticles attach to pathogens selectively, resulting in enhanced sensing with molecular-level specificity.

20 Claims, 6 Drawing Sheets

(52) U.S. Cl.
CPC ..... *G01N 33/497* (2013.01); *G01N 2001/245* (2013.01); *G01N 2033/4975* (2013.01)

(56) References Cited

OTHER PUBLICATIONS

Zhu, Chen, et al., High Temperature and High-Sensitivity Pressure Sensors based on Microwave Resonators, IEEE Sensors Journal, 2021, 11 pages.

Zhu, Chen et al., Metal-organic framework portable chemical sensor, Elsevier, Sensors and Actuators B: Chemical, Jul. 17, 2020, 9 pages, Rolla, Missouri United States.

Zhu, Chen et al., Microwave Device Inspired by Fiber-Optic Extrinsic Fabry-Perot Interferometer: A Novel Ulta-Sensitive Sensing Platform, Journal of Lightwave Technology, vol. 38, No. 34, Dec. 15, 2020, pp. 6961-6966.

Zhu, Chen et al., Probing the Theoretical Ultimate Limit of Coaxial Cable Sensing: Measuring Nanometer-Scale Displacements, IEEE Transactions on Microwave Theory and Techniques, vol. 68, No. 2, Feb. 2020, pp. 816-823.

Zhu, Chen et al., Ultrasensitive Open-Ended Coaxial Cable-Based Microwave Resonator Learns to Sense Impacts, IEEE Transactions on Instrumentation and Measurement, vol. 70, 2021, pp. 9.

* cited by examiner

308 — Biohazard Sprectometer

306 — Chemical Tagger

304 — Radiofrequency Interrogator

302

100 — Aerosol Analyzer

Sample

Air Intake (Sample) → Return Duct in Air Recirculation System (602) → Aerosol Analyzer (100) →

Radiofrequency Interrogator (604)

OPEN-ENDED HOLLOW COAXIAL CABLE RESONATOR SENSOR

CROSS-REFERENCE TO RELATED APPLICATION

This application claims priority from U.S. Provisional Patent Application No. 62/993,277, filed Mar. 23, 2020, the entire disclosure of which is incorporated herein by reference.

STATEMENT REGARDING FEDERALLY SPONSORED RESEARCH OR DEVELOPMENT

This invention was made with government support under: Award #2027571 awarded by the National Science Foundation; Project #3U01HL152410-0251 awarded by the National Institute of Health; and Project #1U01HL152410-01 awarded by the National Institute of Health. The government has certain rights in the invention.

BACKGROUND

Since mid-December 2019, the novel coronavirus 2019 (SARS-CoV-2) has spread to countries around the world and has caused unprecedented public health burdens and panic, especially in dense populations. Unprecedented mitigation strategies have been carried out worldwide to decelerate and degrade the spread of SARS-CoV-2, such as social distancing, sheltering at home, travel restrictions, and even lockdowns of entire countries. The fundamental goal of these mitigation policies is to quarantine confirmed and suspected cases to decrease the encounters between these individuals and healthy people. Accurate, fast, and early detection of possible virus carriers is not only crucial at the time of a pandemic to avoid further widespread infections in the community but is also necessary to prevent the second wave of a pandemic in the reopening stages of world economies. The current "gold standard" method for detecting the SARS-CoV-2 virus is the real-time reverse transcription polymerase chain reaction (rRT-PCR) method, which involves collecting nasopharyngeal swab samples of suspected infectors to obtain body fluids that may contain virions. But, the rRT-PCR method is prone to false negatives due to possible sample loss during sample collection, storage, transfer, test protocols, and the like. Besides, this method is time-consuming and laborious, which means the final binary test result only shows the subject's situation from a few hours or even a few days ago. The test cannot indicate a possible new infection after the sample collection.

The rRT-PCR method strongly depends on the specificity of primers—an artificially designed and synthesized 10-20 bp (base pair) short DNA fragment to initiate the cDNA amplification. Unfortunately, poorly designed primers, as well as problems that may occur during manufacturing, transportation, and storage, may ultimately damage the effectiveness of the primers and cause false negatives in the test results. The difficulties of the rRT-PCR method make on-site and real-time detection of viruses very challenging. Moreover, due to the inadequate number of medical care personnel and the limited instrument resources at compliant laboratories for rRT-PCR testing, the slow identification of COVID-19 makes it very difficult to keep up with the speed of virus transfection in the early- and mid-term stages of disease spread, and prevents notifying subjects of the results in real-time.

In the absence of rapid and reliable detection methods and especially such detection methods for asymptomatic and re-infected individuals, there is an urgent need to develop sensor systems capable of continuously monitoring and detecting possible virus carriers to avoid further widespread infections in the community and to reduce people's uncertainty while waiting for accurate test results.

SUMMARY

Aspects of the present disclosure permit detecting virus carrier individuals through non-invasive, on-demand breath analyses in real-time. A sensor system embodying further aspects detects biohazard aerosol particles to assure biosecurity for high-traffic buildings (airports, seaports, railway stations, hotels, hospitals, shopping malls, amusement parks, community activity centers, etc.). The sensor system enables real-time monitoring of groups of individuals for pathogens (viruses, dangerous bacteria, etc.) and other possibly dangerous substances (chemical mists, pathogenic particles, explosive materials).

In an aspect, an open-ended hollow coaxial cable resonator probe comprises a coaxial structure having an inner conductor and an outer conductor. The coaxial structure has an open input end configured to receive an aerosol sample for analysis. The probe also includes an internal conducting member electrically connecting the inner conductor to the outer conductor to produce a short circuit therebetween and an external conducting surface substantially parallel to a plane defined by the input end of the coaxial structure. The external conducting surface is spaced apart from the input end of the coaxial structure by a dielectric layer that contains the received aerosol sample. The probe further comprises interrogator circuitry coupled to the coaxial structure for transmitting an electromagnetic wave within the coaxial structure. The transmitted electromagnetic wave generates an electric field at the input end of the coaxial structure and the interrogator circuitry is responsive to the generated electric field for determining a resonance frequency of the coaxial structure when the aerosol sample is present in the dielectric layer. The interrogator circuitry is configured to identify virus particles in the aerosol sample as a function of the determined resonance frequency of the coaxial structure. The interrogator circuitry is also configured to identify virus particles in the aerosol sample as a function of the determined impedance parameters of the coaxial structure.

In another aspect, a portable aerosol analyzer comprises an open-ended hollow coaxial cable resonator and a mouthpiece coupled to the resonator through which a subject expels a breath sample into an open end of the resonator. The aerosol analyzer also includes interrogator circuitry coupled to the resonator for transmitting an electromagnetic wave within the resonator. The transmitted electromagnetic wave generates an electric field at an input end of the resonator and the interrogator circuitry is responsive to the generated electric field for determining a resonance frequency and an impedance of the resonator when the breath sample is present in a dielectric layer at the open end of the resonator. The interrogator circuitry is configured to identify virus particles in the breath sample as a function of the determined resonance frequency of the resonator. The interrogator circuitry is also configured to identify virus particles in the aerosol sample as a function of the determined impedance parameters of the coaxial structure.

In yet another aspect, a method of detecting virus particles in an aerosol sample comprises receiving an aerosol sample at an open input end of an open-ended hollow coaxial cable resonator. The resonator includes an inner conductor and an outer conductor, an internal conducting member electrically connecting the inner conductor to the outer conductor to produce a short circuit therebetween, and an external conducting surface substantially parallel to a plane defined by the input end of the resonator and spaced apart from the input end of the coaxial structure by a dielectric layer. The method further comprises containing the received aerosol sample in the dielectric layer, transmitting an electromagnetic wave within the resonator to generate an electric field at the input end of the resonator, and, responsive to the generated electric field, determining a resonance frequency of the resonator when the aerosol sample is present in the dielectric layer. As a function of the determined resonance frequency of the resonator, the method comprises identifying virus particles in the aerosol sample. Alternatively, as a function of the determined impedance of the resonator, the method comprises identifying virus particles in the aerosol sample.

Other objects and features of the present invention will be in part apparent and in part pointed out herein.

BRIEF DESCRIPTION OF THE DRAWINGS

FIG. 3 is a schematic illustration of a sensor system utilizing an open-ended hollow coaxial cable resonator probe according to an embodiment of the present disclosure.

FIG. 5 is a schematic illustration of a wearable electronic breath analyzer probe according to an embodiment of the present disclosure.

FIG. 6 is a schematic illustration of a sensor system for monitoring airborne virus particulates in an enclosed space utilizing an open-ended hollow coaxial cable resonator probe according to an embodiment of the present disclosure.

Corresponding reference characters indicate corresponding parts throughout the drawings.

DETAILED DESCRIPTION

Figure 1A:
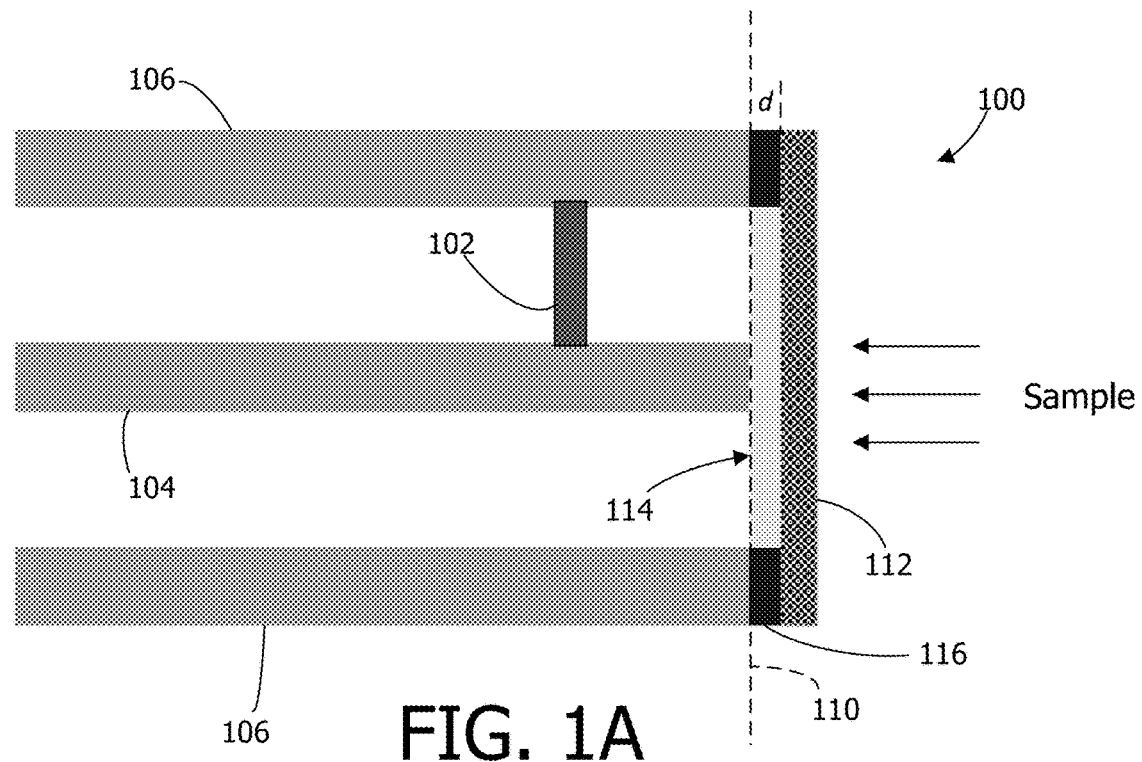
FIGS. 1A and 1B are schematic illustrations of an open-ended hollow coaxial cable resonator probe according to embodiments of the present disclosure.
Figure 1B:
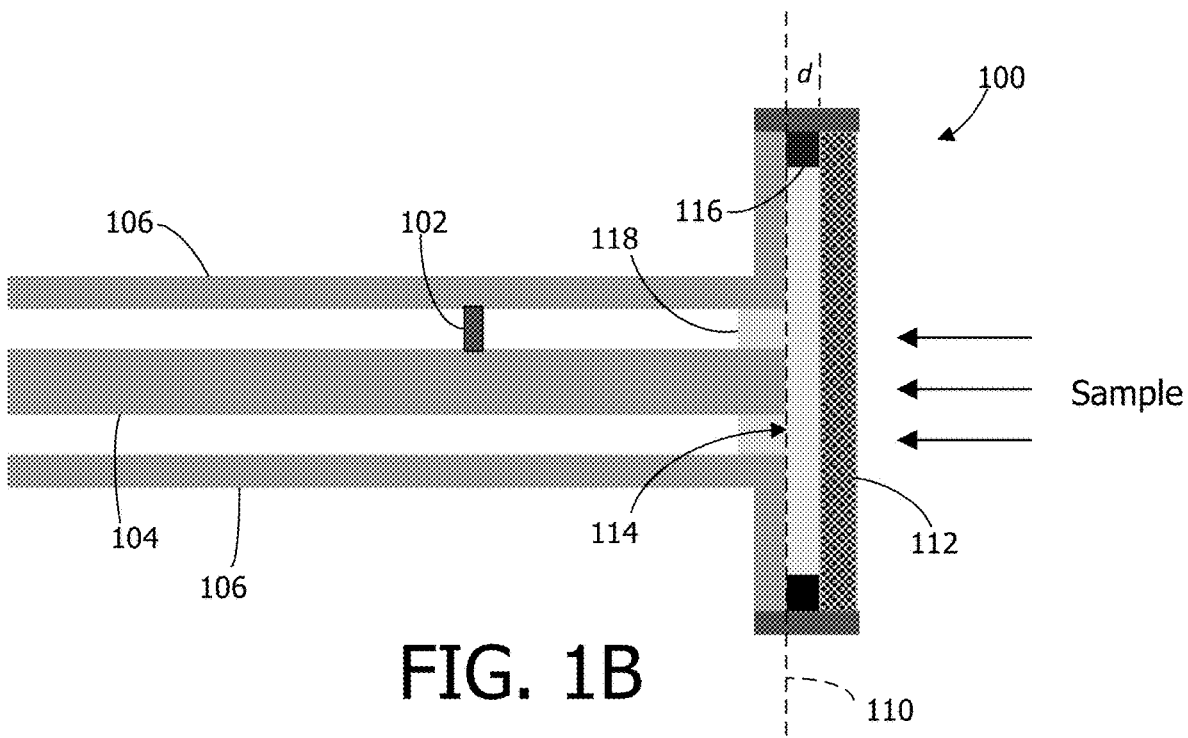

Referring to the drawings, FIGS. 1A and 1B are cross-sectional views of an open-ended hollow coaxial cable resonator (OE-HCCR) probe 100 embodying aspects of the present disclosure. The resonator probe 100 is formed between two microwave reflectors constructed along a coaxial line. The first reflector of the resonating coaxial structure in the illustrated embodiment is a metal post 102 electrically connected by welding or the like at a radio frequency (RF) input end of the coaxial structure. The metal post 102 shorts an inner conductor 104 and an outer conductor 106, which causes a large impedance mismatch and serves as the first reflector of the resonator probe 100. The second reflector is an open end 110 of the coaxial structure. In the illustrated embodiments, an external conducting surface 112 (e.g., a metal plate) is placed parallel and near the open end 110. In other words, a dielectric 114 (e.g., air) sandwiched between the hollow coaxial cable structure defined by inner and outer conductors 104, 106 and external conducting surface 112 serves as the second reflector of the resonating coaxial structure. The resonance frequency of the open-ended coaxial resonator probe 100 depends strongly on a gap distance between external conducting surface 112 and open end 110 of the coaxial cable, due to a modulation of the phase of the reflection coefficient that characterizes the open end.

In one embodiment, OE-HCCR probe 100 comprises a stainless steel hollow coaxial cable, which offers strong mechanical strength and the capability for use at high temperatures. The OE-HCCR probe 100 in this embodiment has air as the dielectric layer 114 for the transmission line. Hollow coaxial cables with air dielectrics have operational advantages at elevated temperatures where conventional dielectrics, such as polytetrafluoroethylene (PTFE) or polyethylene (PE), are not mechanically and chemically stable for sensing applications in harsh environments. The dielectric layer 114 has a thickness of d and a relative permittivity of $\in_r$. The diameter of the inner conductor 104 is, for example, 6.0 mm; the diameter of the outer conductor 106 is, for example, 14.0 mm. The distance between the metal post 102 and the open end 110 of the coaxial cable is, for example, 75 mm.

Referring further to FIGS. 1A and 1B, the OE-HCCR probe 100 is formed by two electromagnetic (EM) wave reflectors 102, 110 (e.g., metal post and open end, respectively) contained in a hollow RF coaxial line. In an embodiment, external conducting surface 112 comprises a porous metal plate spaced apart from open end 110 by a gap distance of d. An annular spacer 116 (e.g., a gasket) separates external conducting surface 112 from open end 110 and the defined gap distance d. In FIG. 1B, outer conductor 106 forms a flange at the open end 110. In addition, a seal 118 of PTFE, PE, or the like closes the open end 110 of the hollow coaxial structure as shown in FIG. 1B.

The transverse EM mode in OE-HCCR probe 100 excites a fringing electric field at open end 110. As gap distance d decreases, the fringing electric field at open end 110 increases dramatically, which reveals the fundamental basis of OE-HCCR probe 100 for ultra-sensitive bio-sensing applications. The smaller the gap distance d between open end 110 and external conducting surface 112, the larger the electric field, the higher the dependence of OE-HCCR probe 100 on the dielectric property of the sample medium in the gap. From the perspective of an equivalent circuit, open end 110 can be modeled simply by an effective capacitance C.

It is to be understood that gap distance d between external conducting surface 112 and open end 110 of the coaxial cable, which can be monitored by tracking the shift of the resonance frequency, can be correlated to the parameters of interest (e.g., various physical or chemical quantities, pressure, acceleration, force, etc.) to configure OE-HCCR probe 100 to function as a sensor device. By correlating the resonance frequency to gap distance d, OE-HCCR probe 100 is configurable for use as a displacement sensor device. The displacement measurement resolution of OE-HCCR probe 100 is three orders of magnitude greater than that of existing coaxial cable-based displacement sensors within a certain dynamic range (~0.11 mm), affording a resolution that is comparable to fiber optic sensors.

In an embodiment, dielectric layer 114 comprises a thin layer of metal-organic framework (MOF). The thickness of the MOF layer is defined by the thickness of the ring-shaped spacer 116. For example, HKUST-1, or MOF-199, having a thickness of ~200 μm is a suitable dielectric layer 114. The porous metal plate 112 backs the MOF layer and allows a sample to enter into the MOF layer. As an example, the center part of porous metal plate 112 comprises PM-35 permeable steel with pore sizes of 25±15 µm. This embodiment is particularly suited for use as a highly sensitive gas probe.

As an unknown sample, such as an aerosol sample (containing pathogens) from human breath, enters the gap 114 between open end 110 and external conducting surface 112, the effective capacitance C changes because of the dielectric property of the aerosol. The effective capacitance C is inversely related to the gap distance d such that the resonance frequency of the OE-HCCR probe 100 has a greater dependence on the dielectric property of the aerosol sample. Hence, a decrease in the gap distance can enhance the sensitivity of OE-HCCR probe 100 to variations of the dielectric property of an analyte entering the gap, revealing a novel sensitivity enhancement mechanism of the OE-HCCR probe 100 for chemical and biological sensing applications. Two different approaches can be implemented for real-time breath-testing: (1) detection of the physico-chemical signatures of a virus in breath (e.g., biomarkers); and, (2) direct detection of viruses from exhaled aerosols.

Figure 2:
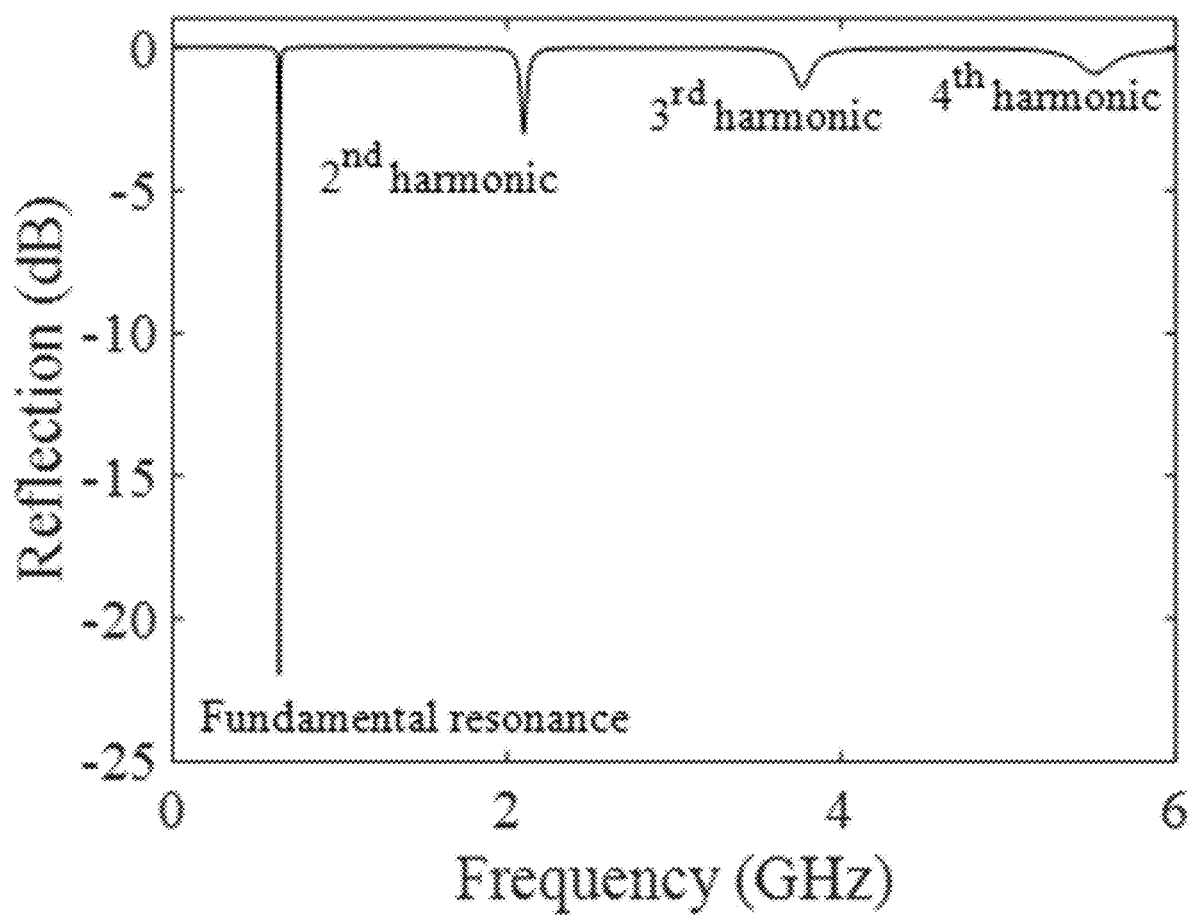
FIG. 2 is a graphical illustration of an example reflection spectrum of an open-ended hollow coaxial cable resonator probe according to an embodiment of the present disclosure.

FIG. 2 plots an example frequency-domain reflection spectrum over a 6 GHz bandwidth for the sensor output of resonator probe 100. In this embodiment, external conducting surface 112 serves as an electric field concentrator and termination plane; the gap between the open end 110 of the coaxial structure and the external conducting surface 112 is filled with dielectric layer 114. As shown in FIG. 2, multiple resonance dips can be observed in the resonator output within the observation frequency bandwidth spanning from 10 MHz to 6 GHz, including the fundamental resonance (~0.636 GHz) and higher-order harmonics (i.e., 2nd, 3rd, and 4th harmonics at 2.100 GHz, 3.767 GHz, and 5.519 GHz, respectively). The fundamental resonance dip provides the highest signal-to-noise ratio and is employed as the reference signal for sensing applications.

FIG. 3 illustrates a sensor system 300 based on OE-HCCR probe 100. The OE-HCCR device platform design can be optimized to detect various physicochemical attributes of the human lung capacity and elements of the composition of the breath aerosol. According to aspects of the present disclosure, the composition of the breath aerosols (water, virus, bacterial) correlates to permittivity signatures that can be extracted using, for example, machine learning algorithms. The front-end probe, OE-HCCR probe 100, is configurable for distinguishing sick and healthy individuals through a rapid and definitive test of an individual's breath obtained via a disposable mouthpiece 302. In an embodiment, a radiofrequency interrogation unit 304 is coupled to the OE-HCCR 100 for fast sample analyses. The breath samples are directed to a chemical tagger system 306 for chemical modification if a positive result for poor lung health is determined. Components of disease agents are chemically labeled for detailed analyses by a back-end spectrometer and air concentrator system. The back-end section of the sensor system 300 comprises a THz spectrometer 308 (e.g., Tera-Flash pro available from TOPTICA Photonics Inc.) optimized for detection of specific attributes of disease-causing agents (e.g., SARS-CoV-2, Influenza) and related diseases of the lungs. Machine learning algorithms (e.g., random forest algorithm) are employed to analyze the OE-HCCR aerosol output data and characterize the predictive capabilities of the sensor 300 for identifying diseased individuals.

In another embodiment, a sensor system based on OE-HCCR probe 100 includes a vector network analyzer, such as the Agilent 8753ES, connected via a communication coaxial cable for analyzing the output of the resonator probe 100.

The sensor system 300 is configured to identify possible asymptomatic carriers of the virus rapidly and alarm the surrounding community, which may become infected if unknowingly exposed. As a typical implementation, the sensor system is integrated into a TSA millimeter-wave scanner for first-stage detection of virus-contaminated droplets in human-exhaled air inside a TSA scanner at airport checkpoints. Along with an IR temperature measurement, an individual exhales one to three times through a mouth port (equipped with the disposable mouthpiece 302) that is maintained at negative pressure. The front-end OE-HCCR probe 100 captures and immediately identifies aerosol particles in terms of size and chemical composition with the assistance of trained machine learning algorithms and provides an alert when a possible virus or disease risk is detected. In the case of a positive detection, the individual inside the TSA scanner will remain isolated. Subsequently, the exhaled sample is chemically processed and analyzed for viruses and disease materials using the chemical tagger 306 followed by the THz spectrometer 308. Ultimately, the need for further medical isolation and observation will be assessed. The sensor system 300 has a fast response time (<1 minute), high-throughput capability, portability, low-cost, and is easy to deploy. The sensor system 300 can also be easily integrated into the building air recirculation system to create a complete solution to assess the "biosecurity" level of an entire building.

In operation, negative pressure guides the exhaled contents through the active volume of the probe 100. The dielectric layer 114 in this embodiment comprises a PTFE filter having a small pore size (0.1 µm) capable of trapping the particulate matter contained in the aerosol (such as lung, tracheal, and oral secretions that may contain virions). Different particles intercepted by the filter membrane will have different permittivities due to their different structures, chemical compositions, and molecular configurations, and thus will show specific signal characteristics. These specificities are used to quickly identify key pathogens and related disease-specific signals. The relevant signals increase cumulatively depending on the number of virions of the exhalation batches. When the target is a specific pathogen, the increase in its corresponding signal level facilitates the correct judgment of the disease.

As the aerosol sample passes through the gap 114, the particles replace the air in the gap and serve as the gap medium. Due to the ultra-high sensitivity of the OE-HCCR probe 100 to the dielectric property of the gap medium, OE-HCCR probe 100 exhibits unique time-transient responses to different types of particles with different dielectric constants as well as dimensional sizes. The time-transient signals could be considered as "fingerprint" features that correspond to a set of unique parameters for different particles (e.g., dust, bacteria, coronavirus, etc.). Using state-of-the-art machine learning models (after adequate training) to analyze the "fingerprint" features enables unambiguous one-to-one mapping between the recorded response of OE-HCCR probe 100 and the dielectric property of the aerosol sample provided that the size distribution is determined from an integrated particle size analyzer. Combining the prominent advantages of the particle size analyzer and the OE-HCCR probe 100 offers a comprehensive method of concurrently quantifying the size and composition information for the aerosol sample. Therefore, an aerosol analyzer embodying aspects of the present disclosure is able to identify the droplets with/without the contamination of a virus in the aerosol sample.

Some pathogens have similar protein envelopes and RNA content, which are difficult to distinguish using signal accumulation alone. For this reason, sensor system 300 may be configured to include an immuno-mechanism to improve the ability to recognize target pathogens. In an embodiment, polyclonal and/or monoclonal antibodies against SARS-CoV-2 constitute a special beacon that reduces the disulfide bonds of the antibody's long chain to form sulfhydryl groups to link with gold or other (e.g., $BaTiO_3$) nanoparticles designed as indicator beacons because of anomalous permittivities. An antibody aerosol containing the gold nanoparticle beacon is triggered to be released after the individual exhales. The antibody aerosol is guided into the active sensing volume by negative pressure, where it binds to the antigen-virus particles on the filter. When a certain number of virus particles are specifically conjugated by the antibody, the gold nanoparticles tethered to the end of the antibody sufficiently enhance the permittivity in the sensing area, and this signal enhancement is linearly related to the number of virus particles present in the area. Therefore, it is possible to provide antigen-specific information regarding the health status of the individual.

Figure 4:
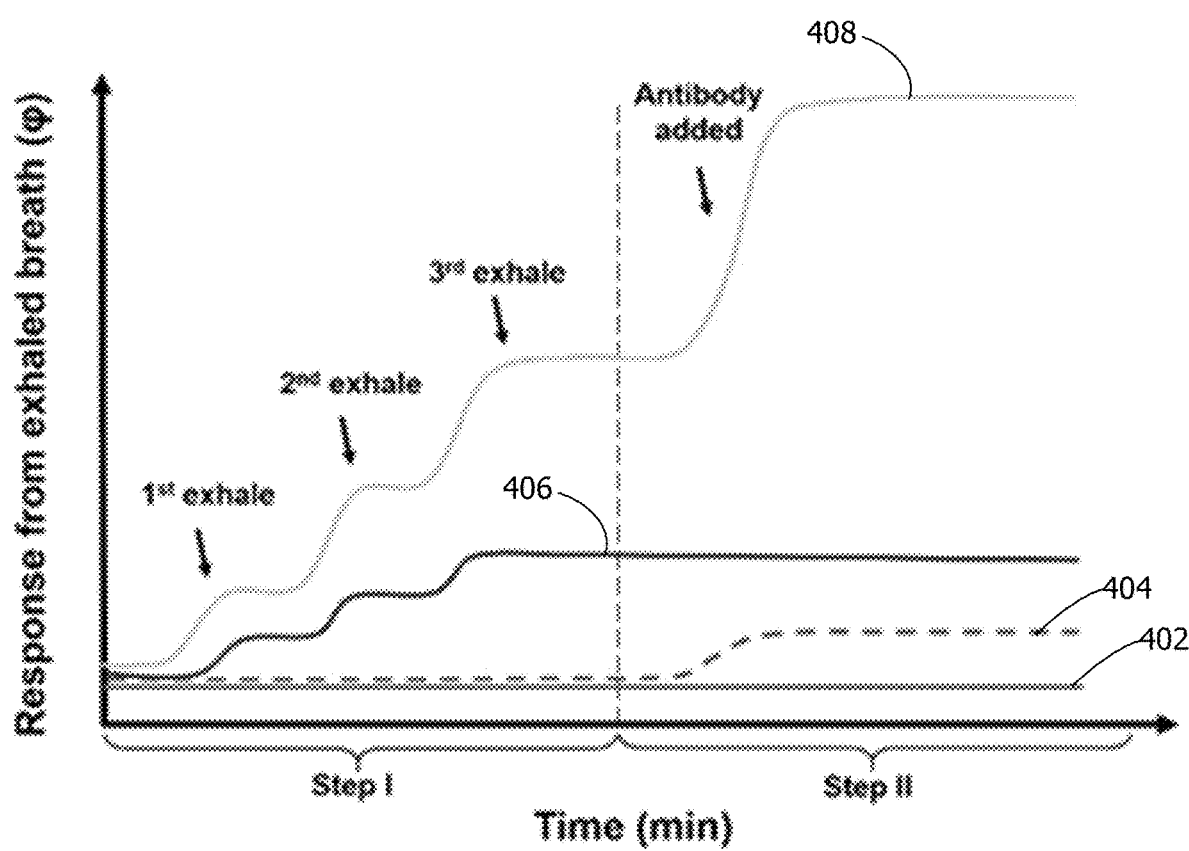
FIG. 4 is a graphical illustration of example profiles of exhaled breath aerosols and the build-up curves for non-volatile solid particulates and for target SARS-CoV-2 viruses according to an embodiment of the present disclosure.

FIG. 4 graphically illustrates example signals that the individual generates from a serial sequence of three deep breaths. Following the serial three-breath sequence, an antibody aerosol is added to confirm the specificity and enhance the probe's output signal for the target virus, such as SARS-CoV-2. The test process is divided into two steps. The first step is the signal that the individual generates during exhalations, which is largely composed of water vapor and carbon dioxide gas. The second step is the prediction result after adding the aerosol with the gold-nanoparticle beacon antibody. A solid line 402 represents healthy individuals who exhale no pathogens and, therefore, whose exhaled breaths accumulate no signal. A dashed line 404 represents asymptomatic infected individuals who carry a limited number of pathogens (low copy number), such that in the first step, almost no accumulation of exhaled matter can be detected. But the addition of the gold-nanoparticle beacon antibody in the second step shows signal enhancement. Therefore, the dashed line 404 provides the first evidence of an asymptomatic person at the earliest stage of infection and should be followed up by additional testing. A solid line 406 indicates that the subject is infected with pathogens other than a target virus, e.g., SARS-CoV-2. Therefore, an accumulation of baseline levels with increasing numbers of exhalations can be observed in the first step. But, in the second step, no further signal growth will be seen because no antibodies and tethered beacons are attached. Finally, a solid line 408 represents symptomatic COVID-19 patients. Clear baseline accumulation can be seen during the first step, and a much higher-level signal will be observed in the second step. This is the evidence that the antibodies and tethered beacons recognize the corresponding antigen, thus confirming that the patient carries the target virions.

Figure 5:
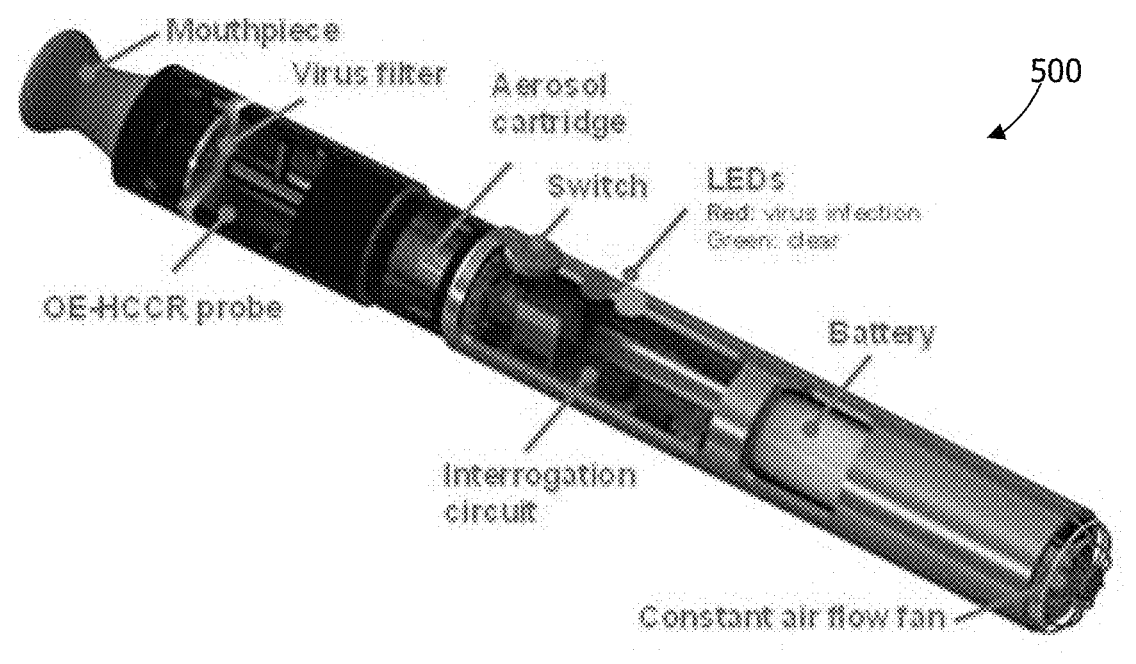

Referring now to FIG. 5, a wearable electronic breath analyzer probe 500 provides real-time identification of asymptomatic and pre-/very early-symptomatic individuals infected with COVID-19 through simple and non-invasive breath testing based on phase-interrogated ultra-sensitive microwave resonance. The breath analyzer probe device 500, which was inspired by the E-cigarette design, is illustrated in FIG. 5. Here, the focus is on the second approach aimed at detecting SARS-CoV-2 and other viruses. The front end of breath analyzer probe 500 comprises ultra-sensitive open-ended hollow coaxial cable resonator probe 100 for analyzing a subject's breath. In this embodiment, a miniaturized interrogation unit based on a portable vector network analyzer is integrated into the breath analyzer probe 500.

A filter (e.g., PTFE or N-95 material) is positioned in the gap 114 between the open end 110 of the coaxial cable and the metal plate 112. The transverse EM mode in the OE-HCCR probe 100 excites a fringing electric field at the open end of the coaxial cable. As the gap distance decreases, the fringing electric field at the open end of the coaxial cable increases dramatically; the smaller the gap distance between open end 110 and the porous metal plate 112, the larger the electric field, and the higher the dependence of the OE-HCCR probe 100 on the dielectric property of the medium (e.g., filter and its contents) in the gap 114.

The dielectric property of the filter is directly encoded into the phase reflection coefficient of the open end 110 of the coaxial resonator probe 100. The collected aerosols from the breath of an infected individual consist of water, carbon dioxide gas, and virus; the filter traps the virus while the constant airflow (e.g., driven by a vacuum) removes the water and carbon dioxide gas components. Thus, the average permittivity of the filter in the active volume of the sensor (i.e., the gap 114) increases due to the inclusion of the virus in its open pores. The increase in the permittivity increases the capacitance at open end 110, thus changing the phase reflection coefficient of the open end of the coaxial cable, which is subsequently amplified by the resonance-based phase-shift-amplification scheme. Minuscule changes in the average relative permittivity of the filter (~0.02 ppb) contained in the OE-HCCR breath analyzer probe, caused by trapping SARS-CoV-2 viruses, can be accurately metered by the ultrahigh-sensitivity microwave resonator.

Unlike the current rRT-PCR method, breath analyzer probe device 500 collects viruses from human breaths from an individual and traps the virus in the active volume using the filter. The collected aerosol of an infected individual consists of water and virus (~1-20 pg per breath). The microfiber grids of the filter retain the virus while the constant airflow (driven by a vacuum) removes the water component. The average permittivity in the active volume of the resonator probe 100 increases with each breath, which can be metered as a build-up curve by the breath analyzer probe 500 that has a limit of detection (LoD) in the sub-pico-gram range (~110 virions), for example. To specify detection of SARS-CoV-2 viruses, specific antibodies, modified with tethered 3-nm gold or other (e.g., $BaTiO_3$) nanoparticles, deployed as an aerosol reactant flow through the analyzer's active volume via an upstream aerosol generator (e.g., Constant Output Atomizer Model 3076 available from TSI, Inc.) after a person exhales. The water vapor carried by the aerosol temporarily infiltrates the filter microgrid and allows the modified antibodies to bind to the immunogenic sites of the trapped viruses in a quasi-liquid environment. A drastic increase in permittivity from the tethered gold or other (e.g., $BaTiO_3$) nanoparticles caused by the accumulation of antibodies in the active volume of the resonator probe 100 can thus be read out and, hence, a quick diagnosis made specifically for SARS-CoV-2 viruses. In this manner, continuously monitoring and detecting virus carrier individuals through simple and non-invasive breath testing, especially for asymptomatic and pre-/very early-symptomatic individuals, avoid bottlenecks in the current testing approaches, further widespread infections in the community, and reduce the angst and uncertainty in a nominally healthy population.

The electronic breath analyzer probe 500 is based on direct detection of virus particulate (SARS-CoV-2) from exhaled breath in real-time (time to test result less than 30s) for diagnostic of COVID-19 before onset of symptoms. By collecting multiple breaths, aspects of the present disclosure address the dynamic range, from asymptomatic, pre-/very early-symptomatic, to late-stage symptomatic individuals, with sufficient sensitivity and specificity to accurately predict illness. Moreover, breath analyzer probe 500 can be specifically designed using immunology chemistry (antigen-antibody reaction), deployed as an aerosol reactant, to output fingerprint electronic signatures (drastic increases in measured phase from the breath analyzer probe) that uniquely indicate COVID-19. In an embodiment, breath analyzer probe 500 is a passive device and power consumption is only required on demand when the breath analyzer probe is turned on and sampling of breath from the sensor wearer occurs. The device can be self-powered using a rechargeable lithium battery. Real-time interpretation of the test results from the breath analyzer probe 500 can be made straightforward in the sensor design by integrating an LED alarm system. Once the red LED alarms, a subject can be isolated, fully tested, and receive medical attention as necessary. The test results can be automatically saved in an integrated microcomputer in the breath analyzer probe for storage and further data access.

The breath analyzer probe 500 is also applicable to other emerging viral diseases. By simply redesigning the antibody chemistry, the breath analyzer probe can be used to detect corresponding viral diseases based on the same principle and measurement procedures.

The unique ultrasensitivity of the breath analyzer probe 500 for viruses involves a two-amplification process. The first amplification relies on the fringing electric field of the open-ended resonator probe 100, where the mutual capacitance between the open end 110 and a nearby metal plate 112 changes as a function of the dielectric property in the gap 114 between the open end and the metal plate. The second amplification process depends on a destructive interference-based phase-shift amplifier. Immunology chemistry-based strategies are included in the design of the breath analyzer probe that enables the breath analyzer probe with the capability for molecular-level identification of COVID-19 and other pathogens.

The volume of exhaled gas from an individual infected with COVID-19 is approximately 1 L and can contain as much as 20 pg of non-volatile solid particulates (e.g., virions) entrapped in aerosol microdroplets. The SARS-CoV-2 virus has a diameter of approximately 120 nm, a calculated volume of 9.05x10-22 m$^3$, and an approximate molecular mass of 1,000 MDa. Therefore, the maximum number of viruses per human breath from a diseased individual is approximately 12,050 and would occupy a minimum condensed-phase volume of 1.09×10-17 m$^3$ (1.09× 10-8 μL). The OE-HCCR breath analyzer probe 500 preferably has a 6 mm-diameter central conductor (~10 mm-diameter electric field in the active volume) and a 0.127 mm-thick filter gap for operation at critical coupling and has an active sensing volume of 9.97×10−9 m$^3$ (9.97 μL). Commercially available PTFE filter (SKC, Eighty Four, PA) positioned in the OE-HCCR filter gap will trap 90% of the virions in exhaled breath. Therefore, a 9.81×10−18 m$^3$ (9.81×10-9 μL) volume of virions will be trapped in the pores of the filter, corresponding to a volume ratio (i.e., total volume of virions/active sensing volume) of 9.84×10$^{-10}$. Supposing that the initial volume fraction of the air pores in the filter is x, then the volume fraction of PTFE is (1−x). The effective relative permittivity of the filter is given by:

$$E_{initial} = X\varepsilon_{air} + \varepsilon_{PTFE}(1-x) \tag{1}$$

where $\varepsilon_{air}$ and $\varepsilon_{PTFE}$ are the relative permittivity of air and PTFE, respectively. After the viruses replace the air in the open pores, the effective relative permittivity can be expressed as:

$$\varepsilon_{after} = X\varepsilon_{air} + (1-X)\varepsilon_{PTFE} + 9.84 \times 10^{-10} \cdot (\varepsilon_{virus} - \varepsilon_{air}) = \varepsilon_{initial} + 9.84 \times 10^{-10} \cdot (\varepsilon_{virus} - \varepsilon_{air}) \tag{2}$$

where $\varepsilon_{virus}$ is the relative permittivity of the SARS-CoV-2 virus. Consider $\varepsilon_{virus}$ and $\varepsilon_{air}$ to be 3 (a typical value for proteins) and 1, respectively. According to Eq. (2), a single breath from an infected individual causes a 0.00197 ppm change in the relative permittivity of the filter. Given the theoretically-determined sensitivity for detecting changes in relative permittivity employing the OE-HCCR, operated at the critical coupling point, to be −110 deg/ppm, the corresponding phase signal change of the OE-HCCR probe 100 is calculated to be 0.217 deg, which can be unambiguously resolved using a state-of-the-art interrogator with a peak-to-peak noise level of 0.002 deg (signal-to-noise ratio (SNR) of 108). The LoD of the OE-HCCR probe 100 is calculated to be ~110 SARS-Cov-2 viruses with SNR of 1.

It is to be understood that by further decreasing the size of OE-HCCR probe 100, the active sensing volume of the probe also decreases so that a higher filling factor of the SARS-CoV-2 virions in the filter will be obtained. A higher filling factor increases the effective change in the relative permittivity of the filter element, leading to a larger phase change of the OE-HCCR probe 100. An alternative approach to increasing the SNR is to use the method of signal averaging. The SNR increases linearly with the square root of the number of identical measurements that are co-added. For example, it would be advantageous to detect a number of viruses one hundred times smaller than the LoD of the OE-HCCR probe 100. That is, detecting one virus from a shallow breath of an asymptomatic infected individual would require signal averaging 1×10$^4$ measurements of one trapped virus to achieve an SNR of 1 that was previously achieved with one measurement on 12,050 viruses (see above). If the measurement time is 1 millisecond, then 10 seconds would be required to determine if an asymptomatic individual exhaled any virus. Once the viruses are collected, there would be few limitations to signal averaging. Advantageously, a personal device that collects and measures viruses from a single individual's breath is useful for implementing the method of signal averaging. Each additional breath would augment the number of viruses that are trapped in the filter and measured and would decrease the time to obtain sufficient SNR to unambiguously determine the presence of the trapped viruses.

For the OE-HCCR probe 100, a multi-beam interferometer (resonator), its output signal is the summation of multiple signals coupled out at the first reflector (the metal post 102) during multiple round trips of the input signal within the cavity. The amplitude noise of these coupled signals is mutually correlated since they are essentially a portion of the input signal coming from the source. Therefore, the noise amplitude of the input signal does not affect the phase sensitivity. Hence, the point of critical coupling can be used for phase-shift amplification in the OE-HCCR probe 100 even though the amplitude reduction of the output signal is always accompanied. The ultimate limit for the phase resolution of the system based on this technique is determined by the input phase noise and the shot and thermal noise of the detector in the ultra-high amplification regime, e.g., at exactly the point of critical coupling. With a microwave interrogator (e.g., available from Keysight Technologies) that has an amplitude detection limit of −140 dBm and a phase resolution of 0.002°, more than 100,000-fold amplification can be realized in the over-coupling zone at sub-Gigahertz frequencies.

A key feature of the OE-HCCR breath analyzer 500 is that the first-stage dielectric sensitivity and the second-stage phase-shift amplification can be seamlessly integrated to achieve ultra-high sensitivity to changes in the dielectric property of the gap medium. Before reaching the critical coupling, both the first-stage dielectric sensitivity and the second-stage phase-shift amplification factor increase as the gap distance between the open end of the coaxial cable and the metal plate decreases.

In an alternative embodiment, aspects of the present disclosure are incorporated into a building monitoring system for continuous monitoring and identification of airborne SARS-CoV-2 virions in an enclosed space. As shown schematically in FIG. 6, a sensor system 600 provides a new approach for selective and quantitative detection of low virus particle numbers within seconds by employing phase-interrogated ultra-sensitive microwave resonance technology. The ultra-high sensitivity of the probe 100 to changes in the dielectric property (permittivity) of the medium (e.g., filter and its particle contents) in the active volume makes it possible to detect as low as ~110 SARS-Cov-2 viruses per 50 mm$^2$ in real-time. The unique ultrasensitivity of the probe 100 for viruses involves a two-amplification process. The first amplification relies on the fringing electric field of an open-ended resonator, where the mutual capacitance between the open end and a nearby metal plate changes as a function of dielectric property in the gap (active sample volume) between the open end and the metal plate. The second amplification process relies on a destructive interference-based phase-shift amplifier.

As illustrated in FIG. 6, the sensor system 600 is easily integrated into the air circulation system of a building. The system 600 incorporates resonator probe 100 embodied by a robust hollow cylindrical metal radiofrequency waveguide structure, scalable in size up to several feet in diameter, that seamlessly replaces a section of a return duct 602 in the air handling system of an enclosed space, such as a barracks, warship, city building, airplane, etc. A radiofrequency interrogation unit 604 is coupled to the OE-HCCR 100 for fast sample analyses in less than one minute. Unlike the current time-consuming air sample collection and ex-situ PCR testing method, aspects of the present disclosure permit continuous collection and trapping of viruses from the air recirculation system of an enclosed space by integrating a large-scale version of an OE-HCCR in the return duct of an existing air handling system. The sensor system 600 includes a filter (e.g., N95 material used in face masks) in the active volume. The microfiber grids of the filter retain the virus while the constant airflow (driven by the air handling system) removes the water component. The average permittivity in the probe's active volume will increase with the build-up of virus particulates, which can be metered by the OE-HCCR particle analyzer of system 600, with LoD in the sub-pico-gram range. To detect a specific virus, such as SARS-CoV-2, specific antibodies that are tethered to extremely high permittivity nanoparticles (e.g., calcium copper titanate, barium titanate) are deployed as an aerosolized reactant that is injected into the analyzer's active volume via an upstream aerosol generator. The solvent vapor (e.g., water) comprising the aerosol temporarily infiltrates the filter microgrid and allows the modified antibodies to bind to (tag) the immunogenic sites of the trapped viruses in a quasi-liquid environment. A dramatic increase in sample permittivity caused by the accumulation of antibody-tethered-barium titanate nanoparticles in the active volume of the probe can be read out, thus achieving a rapid, continuous, and targeted diagnosis of SARS-CoV-2 viruses. The sensor system 600 is configured to be integrated into the air recirculation system of an indoor environment, such as a military barracks designed to house a large number of military personnel, thereby creating a complete solution to assess the "biosecurity" level of an enclosed space. The sensor system 600 is characterized by a fast response time (<1 min), high-throughput capability, low-cost, and ease of installment in existing air handling systems.

Advantageously, the active surface area of the probe 100 can be scaled up according to the diameter of the coaxial resonator (e.g., 0.5-foot in diameter) such that it can be directly placed in-line with the intake duct of a building's air circulation or heating, ventilation, and cooling (HVAC) system, and collect viruses from the entire building. For a 20,000 ft$^2$ military barracks and a typical 15 cfm/100 ft$^2$ venting system, the overall air circulation rate is approximately 3,000 cfm or 85,000 L/min. Provided the time allocated to detect viruses is one minute, it is possible to capture and analyze 85,000 viruses from indoor air with a virus concentration of 1 virion/L. The sensitivity of sensor system 600 is approximately 0.5 particle/L, which is two times greater than the Threshold Metric of current Federal requirements (1 particle/L). Within five minutes, system 600 can meet an objective metric of 0.1 particle/L.

In another alternative embodiment, portable open-ended hollow coaxial cable resonator (OE-HCCR) probe 100 provides direct relative humidity (RH) measurements without the assistance of any humidity-sensitive material.

A sensor system with ultra-high sensitivity, high resolution, a rapid response time, and a high signal-to-noise ratio can produce raw data that are exceedingly rich in information, including signals that have the appearances of "noise". The "noise" features directly correlate to measurands of dielectric materials in physical spaces. The use of machine learning techniques to extract useful meanings from the rich information afforded by the ultra-sensitive sensors may offer the potential for probing mundane events for novel embedded phenomena.

Embodiments of the present disclosure may comprise a special-purpose computer including a variety of computer hardware, as described in greater detail below.

For purposes of illustration, programs and other executable program components may be shown as discrete blocks. It is recognized, however, that such programs and components reside at various times in different storage components of a computing device, and are executed by a data processor(s) of the device.

Although described in connection with an exemplary computing system environment, embodiments of the aspects of the invention are operational with other special-purpose computing system environments or configurations. The computing system environment is not intended to suggest any limitation as to the scope of use or functionality of any aspect of the invention. Moreover, the computing system environment should not be interpreted as having any dependency or requirement relating to any one or combination of components illustrated in the exemplary operating environment. Examples of computing systems, environments, and/or configurations that may be suitable for use with aspects of the invention include, but are not limited to, personal computers, server computers, hand-held or laptop devices, multiprocessor systems, microprocessor-based systems, set-top boxes, programmable consumer electronics, mobile telephones, network PCs, minicomputers, mainframe computers, distributed computing environments that include any of the above systems or devices, and the like.

Embodiments of the aspects of the invention may be described in the general context of data and/or processor-executable instructions, such as program modules, stored one or more tangible, non-transitory storage media and executed by one or more processors or other devices. Generally, program modules include, but are not limited to, routines, programs, objects, components, and data structures that perform particular tasks or implement particular abstract data types. Aspects of the invention may also be practiced in distributed computing environments where tasks are performed by remote processing devices that are linked through a communications network. In a distributed computing environment, program modules may be located in both local and remote storage media, including memory storage devices.

In operation, processors, computers and/or servers may execute the processor-executable instructions (e.g., software, firmware, and/or hardware) such as those illustrated herein to implement aspects of the invention.

Embodiments of the aspects of the invention may be implemented with processor-executable instructions. The processor-executable instructions may be organized into one or more processor-executable components or modules on a tangible processor-readable storage medium. Aspects of the invention may be implemented with any number and organization of such components or modules. For example, aspects of the invention are not limited to the specific processor-executable instructions or the specific components or modules illustrated in the figures and described herein. Other embodiments of the aspects of the invention may include different processor-executable instructions or components having more or less functionality than illustrated and described herein.

The order of execution or performance of the operations in embodiments of the aspects of the invention illustrated and described herein is not essential, unless otherwise specified. That is, the operations may be performed in any order, unless otherwise specified, and embodiments of the aspects of the invention may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively, or in addition, a component may be implemented by several components.

The above description illustrates the aspects of the invention by way of example and not by way of limitation. This description enables one skilled in the art to make and use the aspects of the invention, and describes several embodiments, adaptations, variations, alternatives, and uses of the aspects of the invention, including what is presently believed to be the best mode of carrying out the aspects of the invention. Additionally, it is to be understood that the aspects of the invention are not limited in their application to the details of construction and the arrangement of components set forth in the following description or illustrated in the drawings. The aspects of the invention are capable of other embodiments and of being practiced or carried out in various ways. Also, it will be understood that the phraseology and terminology used herein are for the purpose of description and should not be regarded as limiting.

Having described aspects of the invention in detail, it will be apparent that modifications and variations are possible without departing from the scope of aspects of the invention as defined in the appended claims. It is contemplated that various changes could be made in the above constructions, products, and processes without departing from the scope of aspects of the invention. In the preceding specification, various preferred embodiments have been described with reference to the accompanying drawings. It will, however, be evident that various modifications and changes may be made thereto, and additional embodiments may be implemented, without departing from the broader scope of the aspects of the invention as set forth in the claims that follow. The specification and drawings are accordingly to be regarded in an illustrative rather than restrictive sense.

In view of the above, it will be seen that several advantages of the aspects of the invention are achieved, and other advantageous results attained.

The Abstract and Summary are provided to help the reader quickly ascertain the nature of the technical disclosure. They are submitted with the understanding that they will not be used to interpret or limit the scope or meaning of the claims. The Summary is provided to introduce a selection of concepts in simplified form that are further described in the Detailed Description. The Summary is not intended to identify key features or essential features of the claimed subject matter, nor is it intended to be used as an aid in determining the claimed subject matter.

What is claimed is:

1. An open-ended hollow coaxial cable resonator probe comprising:
   a coaxial structure comprising an inner conductor and an outer conductor, the coaxial structure having an open input end configured to receive an aerosol sample for analysis;
   an internal conducting member electrically connecting the inner conductor to the outer conductor to produce a short circuit therebetween;
   an external conducting surface substantially parallel to a plane defined by the input end of the coaxial structure and spaced apart from the input end of the coaxial structure by a dielectric layer, the dielectric layer containing the received aerosol sample; and
   interrogator circuitry coupled to the coaxial structure for transmitting an electromagnetic wave within the coaxial structure, the transmitted electromagnetic wave generating an electric field at the input end of the coaxial structure and the interrogator circuitry responsive to the generated electric field for determining a resonance frequency and an impedance of the coaxial structure when the aerosol sample is present in the dielectric layer, wherein the interrogator circuitry is configured to identify virus particles in the aerosol sample as a function of the determined resonance frequency and impedance of the coaxial structure.

2. The open-ended hollow coaxial cable resonator probe as set forth in claim 1, further comprising a mouthpiece coupled to the open input end of the coaxial structure through which a subject expels breath into the coaxial structure, wherein the aerosol sample comprises the expelled breath.

3. The open-ended hollow coaxial cable resonator probe as set forth in claim 1, wherein the external conducting surface comprises a porous metal plate.

4. The open-ended hollow coaxial cable resonator probe as set forth in claim 1, further comprising an annular spacer positioned between the input end of the coaxial structure and the external conducting surface, the annular spacer defining a gap between the input end of the coaxial structure and the external conducting surface.

5. The open-ended hollow coaxial cable resonator probe as set forth in claim 4, wherein the annular spacer has a thickness of less than about 300 mm.

6. The open-ended hollow coaxial cable resonator probe as set forth in claim 4, wherein the annular spacer comprises a gasket.

7. The open-ended hollow coaxial cable resonator probe as set forth in claim 1, wherein the dielectric layer comprises air in the gap between the input end of the coaxial structure and the external conducting surface.

8. The open-ended hollow coaxial cable resonator probe as set forth in claim 1, wherein the dielectric layer comprises polytetrafluoroethylene.

9. The open-ended hollow coaxial cable resonator probe as set forth in claim 1, wherein the coaxial structure is configured for installation in a return air duct.

10. The open-ended hollow coaxial cable resonator probe as set forth in claim 1, wherein the internal conducting member is located within 100 mm of the input end of the coaxial structure.

11. A portable aerosol analyzer comprising;
an open-ended hollow coaxial cable resonator;
a mouthpiece coupled to the resonator through which a subject expels a breath sample into an open end of resonator;
interrogator circuitry coupled to the resonator for transmitting an electromagnetic wave within the resonator, the transmitted electromagnetic wave generating an electric field at an input end of the resonator and the interrogator circuitry responsive to the generated electric field for determining a resonance frequency and an impedance of the resonator when the breath sample is present in a dielectric layer at the open end of the resonator, wherein the interrogator circuitry is configured to identify virus particles in the breath sample as a function of the determined resonance frequency and impedance of the resonator.

12. The portable aerosol analyzer as set forth in claim 11, further comprising a fan for producing a negative air pressure in the resonator to draw the breath from the subject into the resonator.

13. The portable aerosol analyzer as set forth in claim 11, further comprising a filter configured for trapping the virus particles in the breath sample, the filter positioned between the mouthpiece and the open end of the resonator.

14. The portable aerosol analyzer as set forth claim 13, wherein the filter comprises polytetrafluoroethylene.

15. The portable aerosol analyzer as set forth in claim 11, wherein the resonator comprises:
a coaxial structure having an inner conductor and an outer conductor;
an internal conducting member electrically connecting the inner conductor to the outer conductor to produce a short circuit therebetween; and
an external conducting surface substantially parallel to a plane defined by the open end of the coaxial structure and spaced apart from the open end of the coaxial structure by the filter.

16. The portable aerosol analyzer as set forth in claim 15, wherein the external conducting surface comprises a porous metal plate.

17. The portable aerosol analyzer as set forth in claim 15, wherein the internal conducting member is located within 100 mm of the input end of the coaxial structure.

18. A method of detecting virus particles in an aerosol sample comprising:
receiving an aerosol sample at an open input end of an open-ended hollow coaxial cable resonator, the resonator comprising:
an inner conductor and an outer conductor,
an internal conducting member electrically connecting the inner conductor to the outer conductor to produce a short circuit therebetween, and
an external conducting surface substantially parallel to a plane defined by the input end of the resonator and spaced apart from the input end of the coaxial structure by a dielectric layer;
containing the received aerosol sample in the dielectric layer;
transmitting an electromagnetic wave within the resonator to generate an electric field at the input end of the resonator;
responsive to the generated electric field, determining a resonance frequency and an impedance of the resonator when the aerosol sample is present in the dielectric layer; and
identifying virus particles in the aerosol sample as a function of the determined resonance frequency and impedance of the resonator.

19. The method as set forth in claim 18, further comprising introducing selected antibodies against the virus particles in the aerosol sample, wherein the selected antibodies are tethered to a high-permittivity nanoparticle beacon and bind to the virus particles to enhance permittivity thereof in the dielectric layer.

20. The method as set forth in claim 19, further comprising confirming the virus particles in the aerosol sample based on the enhanced permittivity of a gold or barium titanate nanoparticle beacon tethered to the anitbody.

* * * * *